US006617161B2

(12) United States Patent
Luyten et al.

(10) Patent No.: US 6,617,161 B2
(45) Date of Patent: Sep. 9, 2003

(54) SERUM-FREE CELL GROWTH MEDIUM

(75) Inventors: Frank P. Luyten, Kraainem (BE); Ludwig Erlacher, Vienna (AT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/851,921

(22) Filed: May 9, 2001

(65) Prior Publication Data

US 2001/0039050 A1 Nov. 8, 2001

Related U.S. Application Data

(63) Continuation of application No. 09/468,562, filed on Dec. 21, 1999, now abandoned, and application No. PCT/US98/12958, filed on Jun. 22, 1998.
(60) Provisional application No. 60/050,691, filed on Jun. 25, 1997.

(51) Int. Cl.$^7$ .............................. C12N 5/00; C12N 5/08; A01N 63/00
(52) U.S. Cl. ...................... 435/375; 435/325; 435/366; 435/374; 435/383; 435/388; 435/389; 435/404; 435/405; 424/93.7; 424/93.1
(58) Field of Search ..................... 424/93.7; 435/325, 435/366, 374, 375, 383, 384, 388, 389, 404, 405

(56) References Cited

U.S. PATENT DOCUMENTS 5,723,331 A * 3/1998 Tubo et al. .................. 435/366

FOREIGN PATENT DOCUMENTS

| WO | WO 91/10726 | 7/1991 |
| WO | WO 95/00632 | 1/1995 |
| WO | WO 96/14335 | 5/1996 |

OTHER PUBLICATIONS

Aulthouse et al. : Expression of the Human Chondrocyte Phenotype in Vitro; In Vitro Cellular & Development Biology, 1989, vol. 25, No. 7, pp. 659–668.*
Bonaventure et al. Reexpression of Cartilage–Specific Genes by Dedifferentiated Human Articulare Chondrocytes Cultured in Alginate Beads; Experimental Cell Research, 1994, 212, pp. 97–104.*
Harrison et al. Osteogenin Promotes Reexpression of Cartilage Phenotype by Dedifferentiated Articular Chondrocytes in Serum–Free Medium; Bone Cell Bio. (1991) 265, pp. 340–345.*
Zenzius et al. Bone Morphogenic Protein–2 (BMP–2) Maintains the Phenotype of Articular Chondrocytes in Long Term Monolayer Culture; Molecular Biology of the Cell (1995), vol. 6, No. Suppl. pp. 391A.*

Sailor, L. Z., et all, "Recombinant Human Bone Morphogenetic Protein–2 Maintains the Articular Chondrocyte Phenotype in Long–Term Culture", Journal of Orthopaedic Research, 14:937–945 (1996).
Bang, et al., Growth, Differentiation and the $\beta$–Adrenergic Signal System of HL–60 Cells; Biochemical Pharmacology 38(21):3723–3729 (1989).
Chang, et al., Cartilage–derived Morphogenetic Proteins; J. of Biological Chemistry 269(45):28227–28234 (1994).
Chen, et al., Osteogenic protein–1 promotes growth and maturation of chick sternal chondrocytes in serum–free cultures; J. of Cell Science 106:105–114(1995).
Harrison, et al., Osteogenin Promotes Reexpression of Cartilage Phenotype by Dedifferentiated Articular Chondrocytes in Serum–Free Medium; Experimental Cell Research 192:340–345 (1991).
Hodgson, et al., Fetal Bovine Serum Revisited; Biotechnology 11:49–53 (1993).
Inlow, et al., Insect Cell Culture and Baculovirus Propagation in Protein–Free Medium; J. of Tissue Cluture Methods 12(1):13–16 (1989).
Kunkel, T.A., Rapid and efficient site–specific mutagenesis without phenotypic selection; Proc. Natl. Acad. Sci. USA 82:488–492 (1985).
Labarca, et al., A Simple, Rapid, and Sensitive DNA Assay Procedure; Analytical Biochemistry 102:344–352 (1980).
Luyten, et al., Recombinant Bone Morphogenetic Protein–4, Transforming Growth Factor–$\beta_1$, and Activin A Enhance the Cartilage Phenotype of Articular Chondrocytes in vitro; Experimental Cell Research 210:224–229 (1994).
Vonen, et al., Effect of a New Synthetic Serum Replacement on Insulin and Somotostatin Secretion From Isolated Rat Pancreatic Islets in Long–Term Culture; J. Tiss. Cult. Meth. 14:45–50 (1992).
Sigma Cell Culture 1994 Catalogue and Price List , p. 219–220 (1994).
ATCC Connection 16(2):5–6 (1996).

* cited by examiner

Primary Examiner—Christopher R. Tate
Assistant Examiner—Patricia Patten
(74) Attorney, Agent, or Firm—Knobbe, Martens, Olson & Bear, LLP

(57) ABSTRACT

A chemically defined-serum free growth medium for the in vitro and ex vivo of cells and cell lines. The medium consists of about a one to one ratio (v/v) of two basal growth media containing $\alpha$-ketoglutarate, insulin, transferrin, selenium, bovine serum albumin, linoleic acid, ceruloplasmin, cholesterol, phosphatidyl-ethanolamine, $\alpha$-tocopherol acid succinate, reduced glutathione, taurine, triiodothyronine, hydrocortisone, parathyroid hormone, L-ascorbic acid 2-sulfate, $\beta$-glycerophosphate, PDGF, EGF and FGF. Chondrocytes, when cultured in this medium in the presence of a cartilage derived morphogenetic protein or bone morphogenetic protein, retain their cartilaginous phenotype.

20 Claims, 1 Drawing Sheet

SERUM-FREE CELL GROWTH MEDIUM

RELATED APPLICATIONS

This application is a continuation of U.S. pat. appl. Ser. No. 09/468,562, filed Dec. 21, 1999 now abandoned, which claims the benefit and is a continuation of priority of International Appl. No. PCT/US98/12958, filed Jun. 22,1998, which claims the benefit of priority of U.S. Appl. No. 60/050,691, filed Jun. 25,1997.

FIELD OF THE INVENTION

The present invention relates to a cell growth medium. More specifically, the invention relates to a chemically defined serum-free growth medium useful for the expansion of primary cells or cell lines in culture.

BACKGROUND OF THE INVENTION

Culturing of mammalian cells is an essential technique for research into cellular processes, production of recombinant therapeutic proteins, and generation of expanded cells for transplantation purposes. Cell culture studies have led to the determination of numerous metabolic processes and the identification of growth factors, hormones and their receptors (*Bio Techniques*, 5:534–542, 1987).

The composition of media used to culture cells is of paramount importance because of its influence on cell survival and cell response to various effectors. Conventional cell culture media comprise basal nutrient media supplemented with serum from various sources, most often fetal bovine serum, horse serum or human serum. However, the use of serum is undesirable for several reasons. Growth media containing serum may vary in composition, hormone content, and contaminants, thereby introducing extraneous factors and/or infections agents into the culture system (*Bio Technology*, 11:49–53, 1993; *Pharm. Technol.*, 48:56, 1987). In addition, serum is expensive, impractical for large-scale production of therapeutics. Further, variance between serum lots and laboratory protocols is also a problem. Recent concerns by the FDA, the European community, and others about serum quality, contamination (i.e., bovine spongiform encephalopathy, bovine immunodeficiency virus), and increased demand have generated significant interest in the development and utility of serum-free growth media.

Significant advances have been made in the development of serum substitutes and serum-free media that address the inadequacies of media containing serum (*J. Tissue Cult. Meth.*, 14:45–50, 1992; *Biochem. Pharmacol.*, 38:3723–3729, 1989; *J. Tissue Cult. Meth.*, 12:13–16, 1989). Serum-free media provide many important advantages over serum-containing media, including lot-to-lot consistency, biological uniformity, and freedom from adventitious agents. Serum-free media are generally cost effective and low in protein content. All of these factors contribute to a more controlled examination of cellular, molecular and metabolic processes (*ATCC Connection*, 16(2):5–6, 1996).

Harrison et al. (*Exp. Cell Res.*, 192:340–345, 1991) describe a serum-free medium used for chondrocytes in suspension/agarose cultures. Addition of a cocktail of growth factors to this medium was sufficient to promote colony formation at levels comparable to medium containing 10% fetal bovine serum (FBS).

Serum-free technology is not entirely problem-free. Many serum-free media are highly specific to a particular cell type, are for short-term culturing only, or contain components extracted from serum. Very few available products can support primary cell cultures. Ideally, serum-free media should be compatible with various basal media and be useful for primary culturing and long-term maintenance of established cell lines. The present invention provides such a medium.

SUMMARY OF THE INVENTION

One embodiment of the present invention is a cell growth medium consisting essentially of about a 1:1 ratio (v/v) of two basal cell culture media containing effective cell growth-promoting amounts of α-ketoglutarate, ceruloplasmin, cholesterol, phosphatidylethanolamine, α-tocopherol acid succinate, reduced glutathione, taurine, triiodothyronine, hydrocortisone, parathyroid hormone, L-ascorbic acid 2-sulfate, β-glycerophosphate, platelet-derived growth factor (PDGF), epidermal growth factor (EGF) and basic fibroblast growth factor (bFGF). Preferably, the medium contains about: $1\times10^{-4}$ M α-ketoglutarate, 0.25 U/ml ceruloplasmin, 5 μg/ml cholesterol, 2 μg/ml phosphatidylethanolamine, $9\times10^{-7}$ M α-tocopherol acid succinate, 10 μg/ml reduced glutathione, 1.25 mg/ml taurine, $1.6\times10^{-9}$ M triiodothyronine, $1\times10^{-9}$ M hydrocortisone, $5\times10^{-10}$ M parathyroid hormone, 50 μg/ml L-ascorbic acid 2-sulfate, 10 mM β-glycerophosphate, 4 ng/ml PDGF, 10 ng/ml EGF and 10 ng/ml bFGF. Advantageously, the two basal cell culture media are selected from Dulbecco's modified Eagle's medium (DMEM), Ham's F-12, Essential modified Eagle's medium (EMEM) and RPMI-1640. The medium described above may further contain at least one cartilage derived morphogenetic protein. Preferably, the cartilage derived morphogenetic protein is CDMP-1 or CDMP-2. Advantageously, the medium further contains at least one bone morphogenetic protein. Preferably, the bone morphogenetic protein is OP-1.

The present invention also provides a method of growing or expanding cells or cell lines, comprising contacting the cells with a cell growth medium consisting essentially of about a 1:1 ratio (v/v) of two basal cell culture media containing effective cell growth-promoting amounts of α-ketoglutarate, ceruloplasmin, cholesterol, phosphatidylethanolamine, α-tocopherol acid succinate, reduced glutathione, taurine, triiodothyronine, hydrocortisone, parathyroid hormone, L-ascorbic acid 2-sulfate, β-glycerophosphate, platelet-derived growth factor, epidermal growth factor and basic fibroblast growth factor. Preferably, the cells are primary cells. In one aspect of this preferred embodiment, the cells are chondrocytes or marrow stromal fibroblasts. Advantageously, the cells are grown in vitro. Alternatively, the cells are grown ex vivo.

Another embodiment of the present invention is a method of maintaining a cartilaginous phenotype in chondrocytes in vitro, comprising culturing the chondrocytes in serum-free medium comprising a cartilage-derived morphogenetic protein and/or bone morphogenetic protein.

The present invention also provides a method of repairing a joint surface defect in a mammal in need thereof, comprising the steps of:

isolating normal cartilage in the vicinity of the surface defect;

isolating chondrocytes from the cartilage;

culturing the chondrocytes in serum-free medium comprising a cartilage-derived morphogenetic and/or bone morphogenetic protein whereby the chondrocytes are expanded; and implanting the expanded chondrocytes into the surface defect.

Preferably, the serum-free medium is the medium described above. Advantageously, the step of isolating chondrocytes comprises digestion of cartilage with collagenase.

DETAILED DESCRIPTION OF THE PREFERRED EMBODIMENTS

Figure 1:
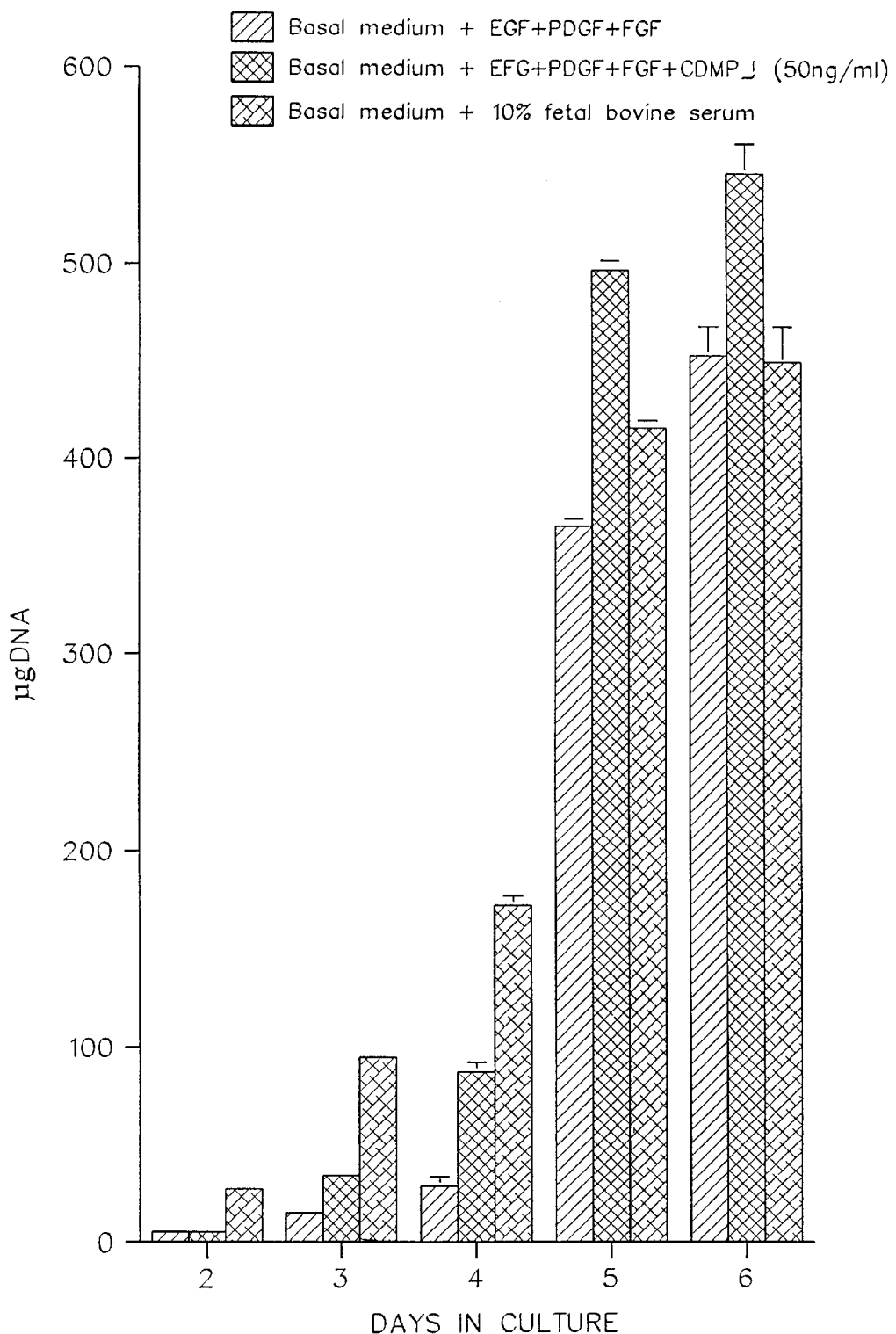
FIG. 1 is a graph showing human fetal chondrocyte expansion as monolayer cultures in the serum-free medium of the invention (basal medium+EGF+PDGF+FGF), the serum-free medium+cartilage-derived morphogenetic protein 1 (CDMP-1), or basal medium containing 10% fetal bovine serum.

The present invention provides a chemically defined serum-free medium which can be used to maintain and expand cells, primary cells and cell lines both in vitro and ex vivo. The medium can be used for any desired cell type, and can be used for both short-term and long-term culturing of cells. The medium consists of two basal cell culture media (about 1:1, v/v) (Collaborative Biomedical Products, Bedford, Mass.; GIBCO/BRL, Gaithersburg, Md.) containing effective cell growth-promoting amounts of insulin, transferrin, selenium, bovine serum albumin, linoleic acid, α-ketoglutarate, ceruloplasmin, cholesterol, phosphatidylethanolamine, α-tocopherol acid succinate, reduced glutathione, taurine, triiodothyronine, hydrocortisone, parathyroid hormone, L-ascorbic acid 2-sulfate and β-glycerophosphate. The medium also contains platelet-derived growth factor (PDGF)-AB or BB, epidermal growth factor (EGF) and basic fibroblast growth factor (bFGF). All supplements are available from Sigma Chemical Co., St. Louis, Mo. Growth factors are available from, for example, Collaborative Medical Products.

Although Ham's F-12/Dulbecco's modified Eagle's medium (DMEM) (about 1:1) are the two preferred basal media, the use of other basal media combinations is also contemplated, including Essential modified Eagle's medium (EMEM) and RPMI-1640. In a preferred embodiment, the concentrations of the compounds listed above are about:

TABLE 1

| Compound | Concentration |
| --- | --- |
| α-ketoglutarate | $1 \times 10^{-4}$ M |
| insulin | 6.25 μg/ml |
| transferrin | 6.25 μg/ml |
| selenium | 6.25 ng/ml |
| bovine serum albumin | 1.25 mg/ml |
| linoleic acid | 5.35 μg/ml |
| ceruloplasmin | 0.25 U/ml |
| cholesterol | 5 μg/ml |
| phosphatidylethanolamine | 2 μg/ml |
| α-tocopherol acid succinate | $9 \times 10^{-7}$ M |
| reduced glutathione | 10 μg/ml |
| taurine | 1.25 μg/ml |
| triiodothyronine | $1.6 \times 10^{-9}$ M |
| hydrocortisone | $1 \times 10^{-9}$ M |
| parathyroid hormone | $5 \times 10^{-10}$ M |
| L-ascorbic acid 2-sulfate | 50 μg/ml |
| β-glycerophosphate | 10 mM |
| PDGF-AB or -BB | 4 ng/ml |
| EGF | 10 ng/ml |
| bFGF | 10 ng/ml |

Although the preferred concentration of each component is as listed in Table 1, these concentrations can be adjusted to suit any desired cell or cell line. This serum-free medium comprises basal medium (BM) plus various components and growth factors. The medium is suitable for anchorage-dependent growth of cells for laboratory experimentation, for large-scale production of recombinant proteins and for expansion of cells for transplantation or implantation. For example, fetal or adult pancreatic islet cells can be expanded in vitro in the serum-free medium of the invention using standard cell culture techniques, then implanted into a diabetic patient. The medium can also be used to effectively culture marrow stromal fibroblasts which differentiate into bone cells.

The medium can also be used to expand chondrocytes as discussed in Example 1. This will allow in vivo cartilage repair. In this embodiment, cartilage is removed from a non-damaged cartilage area around a damage site and digested with collagenase. The resulting chondrocytes are expanded ex vivo in the serum-free medium of the invention, then injected or implanted into the cartilage defect site. Similarly, marrow stromal fibroblasts can be isolated from a normal area adjacent a bone defect, expanded ex vivo in serum-free medium and administered at the site of a bone defect.

The expansion of chondrocytes (articular or fetal limb) in the serum-free medium of the invention containing PDGF, EGF and FGF results in the loss of two main cartilage-specific phenotypic markers, type II collagen and proteoglycan aggrecan, which contribute to the maintenance of the cartilaginous phenotype. These molecules are critical to extracellular matrix synthesis. Chondrocytes cultured in this serum free medium are fibroblastic in appearance and longitudinal in shape, compared to the their typical round morphology. The presence of these two phenotypic markers is important, because the Food and Drug Administration (FDA)/Center for Biologics Evaluation and Research (CBER) requires that protocols relating to ex vivo expansion of articular chondrocytes for repair of joint surfaces prove that the expanded cell populations are very similar to the native chondrocytes. This can be assessed by evaluating the expression of proteoglycan aggrecan and type II collagen at the end of the expansion protocol by Northern blotting, immunoblotting or fluorescence-activated cell sorting (FACS).

In vitro studies were performed to investigate the role of Bone Morphogenetic Proteins/Cartilage-Derived Morphogenetic Proteins (BMPs/CDMPs) in maintaining the cartilaginous phenotype of human articular and fetal limb chondrocytes under serum-free conditions using Ham's F-12/DMEM (1:1) containing the compounds listed in Table 1. One such BMP is osteogenic protein-1 (OP-1; also called BMP-7) (Creative Biomolecules). The inclusion of CDMP-1 and/or OP-1, both at 50 ng/ml in the serum-free medium contributed to the maintenance and re-expression of proteoglycan aggrecan and type II collagen in cultured human fetal chondrocytes as determined by northern blotting of mRNA using labeled cDNA probes to type II collagen and proteoglycan aggrecan. It is contemplated that the inclusion of one or more CDMPs (CDMP-1, CDMP-2) and/or one or more BMPs (i.e. OP-1, BMP-2, BMP-3, BMP-4, BMP-5, BMP-6) ) in any serum-free medium capable of supporting cell growth will contribute to the maintenance of the cartilaginous phenotype and the proteoglycan aggrecan and type II collagen markers.

In addition, other cell types and cell lines in monolayer cultures survived in the serum-free medium containing growth factor cocktail (PDGF, EGF, FGF) with or without CDMPs (i.e., mouse ATDC5 embryonic teratinocarcinoma cells; mouse calvarial osteoblastic clonal cell line MC3T3-E1; the mouse myoblast cell line C2C12; R mutant Mv1 Lu cells; and the rat osteoprogenitor-like cell line ROB-C26), and some continued to proliferate.

The efficacy of cell expansion was compared using Ham's F-12/DMEM (1:1) containing the compounds shown in Table 1 with 10% fetal bovine serum versus the same medium with growth factors (PDGF, FGF and EGF) replacing the serum. Surprisingly, every primary cell or cell line tested with the serum-free medium expanded in culture almost as quickly or equally fast than in the serum-containing medium. This medium will contribute to the reproducibility of cell expansion protocols, provides lot-to-lot consistency, biological uniformity and freedom from adventitious agents. The medium also performs well regardless of the cell type used.

Various CDMP assays performed in cultured cells, including DNA determination, alkaline phosphatase activity and proteoglycan biosynthesis could only be performed in the serum-free medium of the invention; the presence of serum significantly interfered with these assays. Thus, the serum-free medium is essential to the success of these assays.

The growth of human fetal chondrocytes in the serum-free medium of the invention is discussed in the following example.

EXAMPLE 1

Growth of Human Fetal Chondrocytes in Serum-Free Medium

Human fetal limbs from 52 to 79 day old fetuses were provided by the Laboratory for Human Embryology, Department of Pediatrics, University of Washington, Seattle, Wash. This was approved by the Office of Human Subjects Research, National Institutes of Health. The cartilaginous cores were carefully dissected from the surrounding fetal tissue and the chondrocytes were released by a six hour digestion in 0.2% collagenase B (Boehringer Mannheim, Indianapolis, Ind.) in basal medium lacking growth factors (Table 1) at 37° C. Chondrocytes were cultured in either basal medium containing EGF, PDGF and FGF (Table 1); basal medium containing EGF, PDGF, FGF and 50 ng/ml CDMP-1; or basal medium plus 10% fetal bovine serum for two to six days. Cell expansion at days 2, 3, 4, 5 and 6 was assessed by determination of cellular DNA content using bisbenzimide (Hoechst 33258, Sigma, St. Louis, Mo.) (Labarca et al., *Anal. Biochem.*, 102:344–352, 1980). As shown in FIG. 1, by day 6 in culture, human chondrocytes exhibited the same degree of expansion in either serum-free or serum-containing medium.

EXAMPLE 2

Expression and Purification of CDMPs

The cDNAs encoding CDMP-1 and CDMP-2 were isolated by Chang et al. (*J. Biol. Chem.*, 269:28227–28234, 1994) and are also described in International Publication WO96/14335. A cDNA encoding the mature cdmp-1 was modified for insertion into an *E. coli* expression vector by site directed mutagenesis using the method of Kunkel (*Proc. Natl. Acad. Sci. U.S.A.*, 82:488–492, 1985). Following the pro-domain and in close proximity to the RXXR processing site, a leucine residue was converted to a methionine translational initiation codon with a corresponding NcoI restriction site, while a 3' XhoI site was similarly introduced immediately after the translational stop codon. The NcoI to XhoI fragment containing the open reading frame for mature cdmp-1 was ligated to a tetracycline resistant pBR322-derived expression vector. Fermentation was done in shaker flasks using 2YT medium with addition of indolacrylic acid at the appropriate time for induction of the tryptophan promoter (Nichols et al., *J. Mol. Biol.*, 146:45–54, 1981). Large exclusion bodies containing CDMP-1 accumulated. A cDNA for cdmp-2 was similarly tailored for expression. Since the CDMP-2 expression level was quite low, part of the N-terminal region of the highly expressed cdmp-1 was spliced with the 7-cysteine domain of cdmp-2 at the first cysteine, where both genes share a PstI site. Induced cell cultures (250 ml) were centrifuged (11,000×g, 10 min., 4° C.), followed by resuspension of the cell pellets in 50 ml of 25 mM Tris-HCl, 10 mM EDTA, pH 8.0 (1×TE) containing 100 μg/ml lysozy cell suspensions were incubated overnight at 37° C., chilled on ice and sonicated. Inclusion bodies were isolated by centrifugation (11,000×g, 20 min., 4° C.) and resuspended in 1×TE. The final washed inclusion body pellets were resuspended in 40 ml 1×TE, 15% glycerol and stored at −20° C.

Reduced and denatured inclusion body protein solutions were prepared by dissolving aliquots of pelleted inclusion bodies in 100 mM Tris-HCl, 10 mM EDTA, 6 M guanidine HCl, 10 mM dithiothreitol (DTT), pH 8.0 (final protein concentration of 4–6 mg/ml). The inclusion body protein solutions were incubated at 37° C. for 30 min., then diluted 40-fold with refolding buffer (100 mM Tris, 10 mM EDTA, 1 M NaCl, 2% 3-[3-cholamidopropyl) dimethylammonio]-2-hydroxy-1-propanesulfonic acid (CHAPS), 5 mM reduced glutathione, 2.5 mM oxidized glutathione, pH 8.7). The refolding reactions were incubated for 72 hours at 4° C. The folding reactions were dialyzed extensively against 10 mM HCl, then clarified by centrifugation (11,000×g, 20 min., 4° C.). The solutions were concentrated using a stirred cell concentrator and YM10 MWCO membranes (Amicon). The concentrated proteins were then lyophilized. The lyophilized proteins were resuspended in 0.8 ml 0.1% trifluoroacetic acid (final acetonitrile concentration—30%). The protein solutions were fractionated by semi-preparative C4 Reverse Phase High Performance Liquid Chromatography (HPLC) using a linear acetonitrile gradient (30–70% in 0.1% TFA). Aliquots of each fraction were analyzed by sodium dodecyl sulfate-polyacrylamide gel electrophoresis (SDS-PAGE) using 15% gels under non-reducing conditions after reduction and alkylation. Peak dimer fractions were pooled and concentrations were estimated by UV absorbance spectra obtained at 280 nm. Protein pools were stored at −20° C.

EXAMPLE 3

Repair of Cartilage Defects

An individual with a joint surface (i.e. knee) defect is identified and healthy cartilage surrounding the defect is surgically removed. The cartilage is then digested with collagenase using standard methods to isolate individual chondrocytes. Chondrocytes are cultured in basal medium containing the components listed in Table 1 and containing CDMP-1 and/or CDMP-2. The expanded chondrocytes are tested for the presence of proteoglycan aggrecan and type II collagen markers, then surgically implanted into the joint defect site. Significant improvement in both clinical signs and symptoms as well as repair of the defect of the joint surface occurs in response to this procedure.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of maintaining a cartilaginous phenotype in chondrocytes in vitro comprising contacting a culture comprising chondrocytes, which have not lost and subsequently re-expressed a cartilaginous phenotype, with a serum-free cell growth medium comprising about a 1:1 ratio (v/v) of two basal cell culture media, said medium containing effective cell growth-promoting concentrations of α-ketoglutarate, insulin, transferrin, selenium, bovine serum albumin, linoleic acid, ceruloplasmin, cholesterol, phosphatidylethanolamine, α-tocopherol acid succinate, reduced glutathione, taurine, triiodothyronine, hydrocortisone, parathyroid hormone, L-ascorbic acid 2-sulfate, β-glycerophosphate, platelet-derived growth factor (PDGF), epidermal growth factor (EGF) and basic fibroblast growth factor (bEGF) and at least one morphogenetic protein selected from the group consisting of cartilage-derived morphogenetic proteins and bone morphogenetic proteins, whereby a cartilaginous phenotype is maintained in said chondrocytes in vitro.

2. A method of repairing a joint surface defect in a mammal in need thereof comprising the steps of:
   removing normal cartilage in the vicinity of said surface defect;
   isolating chondrocytes from said cartilage;
   contacting a culture comprising said chondrocytes, which have not lost and subsequently re-expressed a cartilaginous phenotype, with a serum-free cell growth medium comprising about a 1:1 ratio (v/v) of two basal cell culture media, said medium containing effective cell growth-promoting concentrations of α-ketoglutarate, insulin, transferrin, selenium, bovine serum albumin, linoleic acid, ceruloplasmin, cholesterol, phosphatidylethanolamine, α-tocopherol acid succinate, reduced glutathione, taurine, triiodothyronine, hydrocortisone, parathyroid hormone, L-ascorbic acid 2-sulfate, β-glycerophosphate, platelet-derived growth factor (PDGF), epidermal growth factor (EGF) and basic fibroblast growth factor (bEGF) and at least one morphogenetic protein selected from the group consisting of cartilage-derived morphogenetic proteins and bone morphogenetic proteins, whereby a cartilaginous phenotype is maintained in said chondrocytes; and
   implanting said chondrocytes into said surface defect.

3. The method of claim 1 or 2, wherein two basal cell culture media are selected and mixed in equal proportion and wherein said basal cell culture media are selected from the group consisting of Ham's F-12, Dulbecco's modified Eagle's medium (DMEM), Essential modified Eagle's medium (EMEM) and RPMI-1640.

4. The method of claim 1 or 2, wherein said morphogenetic protein is cartilage-derived morphogenetic protein and is selected from the group consisting of CDMP-1 and CDMP-2.

5. The method of claim 1 or 2, wherein said morphogenetic protein is bone morphogenetic protein and is selected from the group consisting of OP-1, BMP-2, BMP-3, BMP-4, BMP-5 and BMP-6.

6. The method of claim 1 or 2, wherein the concentration of α-ketoglutarate is about $1 \times 10^{-4}$ M.

7. The method of claim 1 or 2, wherein the concentration of ceruloplasmin is about 0.25 U/ml.

8. The method of claim 1 or 2, wherein the concentration of cholesterol is about 5 μg/ml.

9. The method of claim 1 or 2, wherein the concentration of phosphatidyl-ethanolamine is about 2 μg/ml.

10. The method of claim 1 or 2, wherein the concentration of α-tocopherol acid succinate is about $9 \times 10^{-7}$ M.

11. The method of claim 1 or 2, wherein the concentration of reduced glutathione is about 10 μg/ml.

12. The method of claim 1 or 2, wherein the concentration of taurine is about 1.25 μg/ml.

13. The method of claim 1 or 2, wherein the concentration of triiodothyronine is about $1.6 \times 10^{-9}$ M.

14. The method of claim 1 or 2, wherein the concentration of hydrocortisone is about $1 \times 10^{-9}$ M.

15. The method of claim 1 or 2, wherein the concentration of parathyroid hormone is about $5 \times 10^{-10}$ M.

16. The method of claim 1 or 2, wherein the concentration of L-ascorbic acid 2-sulfate is about 50 μg/ml.

17. The method of claim 1 or 2, wherein the concentration of PDGF is about 4 ng/ml.

18. The method of claim 1 or 2, wherein the concentration of EGF is about 10 ng/ml.

19. The method of claim 1 or 2, wherein the concentration of bFGF is about 10 ng/ml.

20. The method of claim 2, wherein said isolating chondrocytes step comprises digestion of said cartilage with collagenase.

* * * * *

UNITED STATES PATENT AND TRADEMARK OFFICE
CERTIFICATE OF CORRECTION

PATENT NO.      : 6,617,161 B2
DATED           : September 9, 2003
INVENTOR(S)     : Luyten et al.

It is certified that error appears in the above-identified patent and that said Letters Patent is hereby corrected as shown below:

<u>Title page,</u>
Item [57], ABSTRACT,
Line 2, after "ex vivo" please add -- growth --.

Signed and Sealed this

Third Day of August, 2004

JON W. DUDAS
*Acting Director of the United States Patent and Trademark Office*